April 7, 1953 H. C. SWIM Plant Pat. 1,179
ROSE PLANT
Filed April 4, 1952 2 SHEETS--SHEET 1
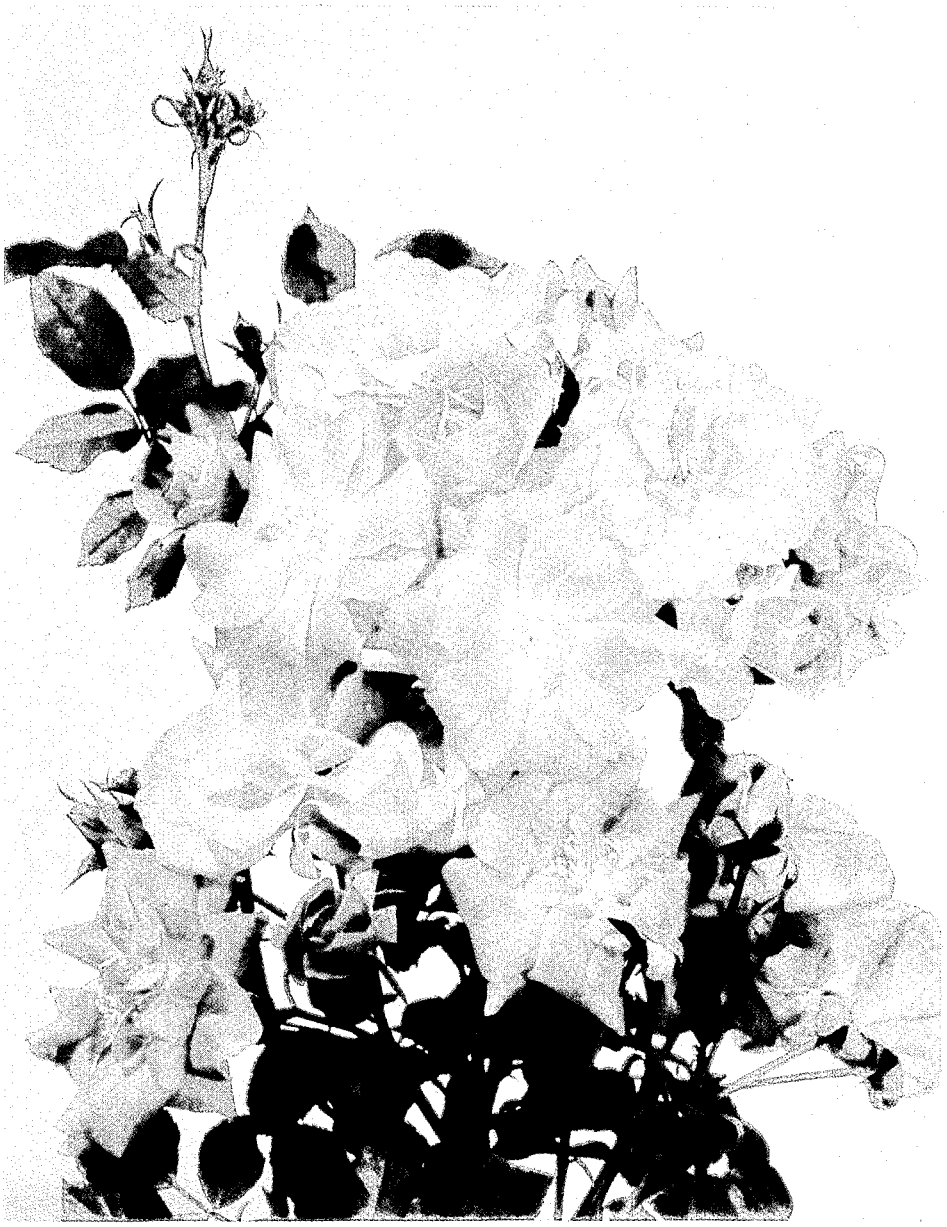
Inventor.
H. C. Swim
By: Robbins & Robbins
Attorneys.

ROSE PLANT
Filed April 4, 1952 2 SHEETS—SHEET 2
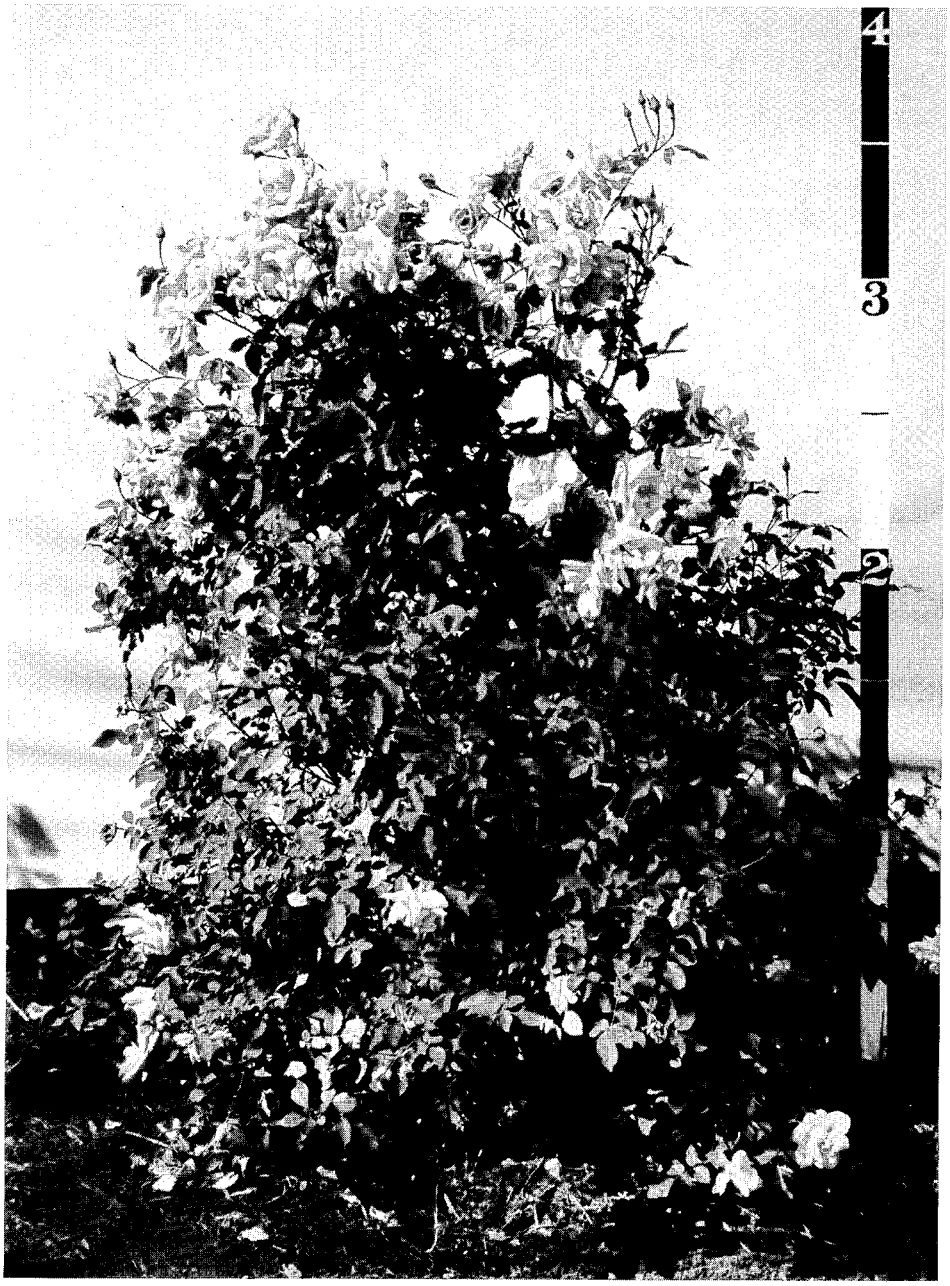
Inventor.
H. C. Swim
By: Robbins Robb
Attorneys.

Patented Apr. 7, 1953

Plant Pat. 1,179

UNITED STATES PATENT OFFICE 1,179

ROSE PLANT

Herbert C. Swim, Ontario, Calif., assignor to Armstrong Nurseries, Inc., Ontario, Calif., a corporation of California Application April 4, 1952, Serial No. 280,484

1 Claim. (Cl. 47—61)

The present invention relates to a new and distinct variety of rose plant of the hybrid polyantha class, originated by crossing the variety "Minna Kordes," known as "World's Fair" in the United States (Plant Patent No. 362) with the variety "Pinnocchio" (Plant Patent No. 484).

The new variety is distinguished from its seed parent "Minna Kordes" by reason of its production of buds and blooms in various shades of pink, whereas "Minna Kordes" produces deep crimson flowers fading to scarlet; the petals and flowers of the present variety are smaller, and the buds have a more slender pointed form than its seed parent; and it produces a greater abundance of foliage which is smaller in size and a lighter shade of green on a more compact plant than "Minna Kordes."

In comparison with the pollen parent, the present variety is distinguished therefrom by its upright-spreading, compact, well-branched habit, and its dull yellow-green foliage, as compared with "Pinocchio's" more spreading habit of growth and production of a deeper green foliage which is less abundant than that of the present new variety. Whereas "Pinocchio" produces sporadic bursts of blooms which are popularly described as pink-suffused salmon, in masses with few or no intervening flowers, this new variety has a notably floriferous nature, and produces blooms continuously throughout the growing season, at times with clusters bunched in compact masses of blooms in various shades of clear pink.

The following unique combination of characteristics distinguish the new variety from all other polyantha varieties, as well as from its parent varieties:

(1) The production of massive clusters of blooms on a vigorous, upright-spreading, well-branched plant which displays an abundance of dull yellow-green foliage;

(2) The pleasing fading reaction, in which the blooms last well under fairly extreme temperature conditions, the petals fading from a dark pink progressively through lighter shades of pink to a very light pinkish white in the mature or aging flower;

(3) The mass effect of the clusters, as viewed as a whole, exhibiting the various stages of flower development from the long pointed dark pink bud to the near white aging bloom.

Asexual reproduction of this new variety by budding at Ontario, California, shows that the foregoing characteristics come true to form and are established and transmitted through succeeding propagations.

In the accompanying drawings, a typical cluster of blooms in various stages of development from bud to fully open bloom is shown in color, and a typical plant having a number of such clusters thereon, as well as a number of individual blooms is shown adjacent to a marker graduated in feet.

The following is a detailed description of the new variety, with color terminology in accordance with Robert F. Wilson's Horticultural Colour Chart, except where Ridgway's Color Standards and Nomenclature are indicated, or where general color terms of ordinary dictionary significance are obvious:

Type: Bush; outdoor; seedling; for cut flowers and for garden decoration.
Class: Hybrid polyantha.
Breeding: Seedling.
*Seed parent.*—"Minna Kordes" ("World's Fair" in the United States).
*Pollen parent.*—"Pinocchio."
Propagation: Holds its distinguishing characteristics through succeeding propagations by budding.

*Flower*

Locality where grown and observed: Ontario, California.
Flowers borne: Usually 5 to 10 or more to stem; in regular, rounded cluster; on strong, medium to long stems.
Quantity of bloom: Very abundant, outdoors.
Continuity: Nearly continuous during growing season.
Fragrance: Slight.
Bud:
*Peduncle.*—Average length; average caliper; sometimes bending; usually erect; usually smooth; some gland-tipped cilia. Color—between Dull Green-Yellow, Plate XVII (Ridgway) and Apple Green, Plate XVII (Ridgway).
*Before calyx breaks.*—Size—small to medium. Form — medium length to long; pointed; with foliaceous appendages, some tomentum, and few gland-tipped cilia on the surface of the bud; usually without bristle-like foliaceous parts extending beyond the tip of the bud.
*As calyx breaks.*—Color—between Neyron Rose, Plate 623, page 76, and Phlox Pink, Plate 625, page 77.
*Sepals.*—Inner surface—with fine, woolly tomentum; margins of alternate sepals have stipitate glands and small appendages; others have woolly tomentum on margin and sometimes stipitate glands with only occasional appendages.

*As first petal opens.*—Size—average. Form—medium length; pointed. Color: outside—near Phlox Pink, Plate 625, page 77, and Phlox Pink, Plate 625/1, page 77; small area at base of petal near Canary Yellow, Plate 2/3, page 2; inside—near Phlox Pink, Plate 625, page 77; small area at base of petal near Canary Yellow, Plate 2/3, page 2.

*Opening.*—Opens up well; is not retarded from opening by cold, hot, wet or dry weather.

Bloom:

*Size, when fully open.*—Small to average; 2¼ inches to 3 inches.

*Petalage.*—Semi-double; from 18 to 23 petals, plus 3 to 6 petaloids; arranged regularly.

*Form.*—High-centered at first; becoming open; petals at first somewhat loosely cupped, with tips rolled outward; becoming later, at maturity, more or less flat, with tips reflexed and lateral margins rolled outward.

Petals:

*Texture.*—Medium thickness; moderately soft; with inside satiny and outside slightly shiny to satiny.

*Shape.*—Outside—obovate with apex usually flat; sometimes with one notch. Intermediate—obovate with apex rounded to flat; sometimes with one notch. Inside—obovate; somewhat irregular, with apex rounded; sometimes with one to two notches.

This description of a newly opened flower was made from a rose grown outdoors in the month of August, at Ontario, California:

*Color.*—Outside petal: outside surface—near Phlox Pink, Plate 625/1, page 77; small area at base of petal near attachment near Canary Yellow, Plate 2/3, page 2; inside surface—near Phlox Pink, Plate 625, page 77; small area at base of petal near attachment near Canary Yellow, Plate 2/3, page 2. Intermediate petal: outside surface—near Phlox Pink, Plate 625/1, page 77; small area at base of petal near attachment near Canary Yellow, Plate 2/3, page 2; inside surface—near Phlox Pink, Plate 625, page 77; small area at base of petal near attachment near Canary Yellow, Plate 2/3, page 2. Inner petal: outside surface—between Phlox Pink, Plate 625, page 77, and Phlox Pink, Plate 625/1, page 77; small area at base of petal near attachment near Canary Yellow, Plate 2/2, page 2; inside surface—near Phlox Pink, Plate 625, page 77; small area at base of petal near attachment near Canary Yellow, Plate 2/2, page 2.

This description was made from a rose that was open for three days outdoors in the month of September, at Ontario, California:

*Color.*—Outside petal: outside surface—between Phlox Pink, Plate 625/2, page 77, and Phlox Pink, Plate 625/3, page 77; area at base of petal near attachment near white; inside surface—Phlox Pink, Plate 625/2, page 77; area at base of petal near attachment near white. Inside petal: outside surface—between Phlox Pink, Plate 625/2, page 77, and Phlox Pink, Plate 625/3, page 77; area at base of petal near attachment near white; inside surface—between Phlox Pink, Plate 625/2, page 77, and Phlox Pink, Plate 625/3, page 77; area at base of petal near attachment near white.

*General color effect.*—Newly opened flower—Phlox Pink, Plate 625, page 77. Three days open—Phlox Pink, Plate 625/2, page 77; area at base near attachment near white.

*Behavior.*—Drop off fairly well except for petaloids, which tend to persist; affected by extremely hot weather as follows; blooms fade more rapidly with tendency for petals to persist after flower is dead.

*Flower longevity.*—On bush in garden—3 to 4 days in September. Cut roses grown outdoors kept at living-room temperatures—3 days in September.

*Reproductive organs*

Stamens: Average number; arranged regularly about pistils.

Filaments: Short to medium length; 4 to 6 mm. long; most with anthers.

Anthers: Small; all open at once approximately. Color: upper side—margins near Indian Yellow, Plate 6/2, page 6; remainder near Aureolin, Plate 3/3, page 3; under side—margins near Indian Yellow, Plate 6/2, page 6; remainder near Aureolin, Plate 3/3, page 3.

Pollen: Moderate amount. Color—near Saffron Yellow, Plate 7/2, page 7.

Pistils: Few to average number; approximately 20 to 25 in number.

Styles: Moderately even; average length; thin to average caliper; somewhat columnar; 8 to 10 mm. long. Color—near Sap Green, Plate 62/3, page 62.

Stigma: Color—near Uranium Green, Plate 63/2, page 63.

Ovaries: Usually all enclosed in calyx.

Hips: Average length for class; ovoid; smooth; walls thick, fleshy. Color (¾ mature)—near Lettuce Green, Plate V (Ridgway) and Aniline Yellow, Plate IV (Ridgway).

Sepals: Nearly permanent; medium length; spear-shaped; recurved. Color: inside—near Biscay Green, Plate XVII (Ridgway); color modified by whitish tomentum; outside—near Biscay Green, Plate XVII (Ridgway).

Seeds: Few to average number; medium size; 6 to 12 in number.

*Plant*

Foliage:

*Leaves.*—Compound of usually 5 to 7 leaflets; abundant; small to medium size; moderately leathery and semi-glossy.

*Leaflets.*—Shape—ovoid with apex acute. Base—round. Margin—doubly serrate.

*Color.*—Mature: upper surface—near Deep Dull Yellow-Green, (2) Plate XXXII (Ridgway); under surface—near Light Grape Green, Plate XLI (Ridgway). Young: upper surface—near Light Cress Green, Plate XXXI (Ridgway), overlaid with near Mineral Red, Plate XXVII (Ridgway); under surface—between Dark Vinaceous, Plate XXVII (Ridgway), and Hydrangea Red, Plate XXVII (Ridgway).

*Rachis.*—Average size. Upper side—grooved, with many stipitate glands on edges. Under side—moderately prickly and with stipitate glands.

*Stipules.*—Medium length; medium width; with medium length to long points, turning out at an angle of less than 45°.

*Disease.*—More than average resistance to mildew when compared with other hybrid polyantha varieties under field or garden conditions.

Growth:

*Habit.*—Upright-spreading; much-branched.

*Growth.*—Vigorous.

*Canes.*—Medium caliper.

*Main stems.*—Color—near Courge Green, Plate XVII (Ridgway). Large prickles—several; medium length; hooked slightly downward; with medium length, narrow base; color—near Tawny-Olive, Plate XXIX (Ridgway). Small prickles—none. Hairs—none.

*Branches.*—Color—between Courge Green, Plate XVII (Ridgway) and Biscay Green, Plate XVII (Ridgway). Large prickles—several; medium length; hooked slightly downward; with medium length, narrow base; color—between Deep Sea-Foam Green, Plate XXXI (Ridgway) and Chrysolite Green, Plate XXXI (Ridgway). Small prickles—none. Hairs—none.

*New shoots.*—Color near Oil Green, Plate V (Ridgway). Large prickles—several; medium length; hooked slightly downward; with medium length, narrow base; color—near Vinaceous-Brown, Plate XXXIX (Ridgway). Small prickles—none. Hairs—none.

I claim:

A new and distinct variety of rose plant of the hybrid polyantha class, substantially as herein shown and described, characterized as to novelty particularly by its vigorous, upright-spreading, well-branched habits of growth, its abundance of dull yellow-green foliage, its production of massive clusters of blooms, the fading reaction of its blooms from a dark pink progressively through lighter shades of pink to a very light pinkish white in the mature or aging flowers, the mass effect of the clusters when viewed as a whole, exhibiting the various stages of flower development from long pointed dark pink bud to near white aging bloom, and the well-lasting quality of the blooms under extreme temperature conditions.

HERBERT C. SWIM.

No referenced cited.